(12) United States Patent
Naegerl

(10) Patent No.: US 7,601,177 B2
(45) Date of Patent: Oct. 13, 2009

(54) METHOD FOR DETERMINING AND ADJUSTING THE OPTIMAL RELATIVE POSITION OF A FUNCTIONAL SURFACE OF AN ARTIFICIAL JOINT

(75) Inventor: Hans Naegerl, Gleichen (DE)

(73) Assignee: HJS Gelenk System GmbH, Munich (DE)

( * ) Notice: Subject to any disclaimer, the term of this patent is extended or adjusted under 35 U.S.C. 154(b) by 100 days.

(21) Appl. No.: 11/531,625

(22) Filed: Sep. 13, 2006

(65) Prior Publication Data
US 2007/0061014 A1    Mar. 15, 2007

(30) Foreign Application Priority Data
Sep. 14, 2005    (DE) .................. 10 2005 044 044

(51) Int. Cl.
*A61F 2/38* (2006.01)
*A61F 2/28* (2006.01)
*A61F 2/00* (2006.01)

(52) U.S. Cl. .................. 623/20.31; 623/23.47; 606/102

(58) Field of Classification Search .............. 623/20.31, 623/23.47, 38, 908, 914; 606/86 R, 87, 88, 606/102
See application file for complete search history.

(56) References Cited

U.S. PATENT DOCUMENTS 5,127,420 A * 7/1992 Horvath ...................... 600/595
5,656,785 A    8/1997 Trainor et al.
6,002,859 A    12/1999 DiGioia, III et al.
2003/0109929 A1    6/2003 Keller
2005/0059980 A1    3/2005 Overes
2005/0101966 A1    5/2005 Lavallee
2005/0177169 A1    8/2005 Fisher et al.
2005/0267600 A1 * 12/2005 Haberman et al. ............ 623/38

FOREIGN PATENT DOCUMENTS

| DE | 10231538 | 10/2003 |
| EP | 1321116 | 6/2003 |
| EP | 1402855 | 3/2004 |
| EP | 1491166 | 12/2004 |
| FR | 2684870 A1 * | 6/1993 |
| WO | WO-9709939 | 3/1997 |
| WO | WO-9820816 | 5/1998 |
| WO | WO-9841152 | 9/1998 |
| WO | WO-2004041097 | 5/2004 |

* cited by examiner

*Primary Examiner*—Thomas J Sweet
*Assistant Examiner*—Yashita Sharma
(74) *Attorney, Agent, or Firm*—Darby & Darby

(57) ABSTRACT

An apparatus and a method for determining and adjusting the optimal relative position of several functional surfaces of a condyle or of a socket of a human or artificial joint, especially for use with an endoprosthesis for the human knee joint, is provided. The apparatus is furnished with a compartment that is moveable by means of a sliding guide relative to a receptacle that can be detachably affixed to a human joint or bone region. A reference position of the compartment—relative to the receptacle—resulting from the posterior-anterior and/or medial-lateral motion of the knee joint can be established using by a marking having a scale.

6 Claims, 1 Drawing Sheet

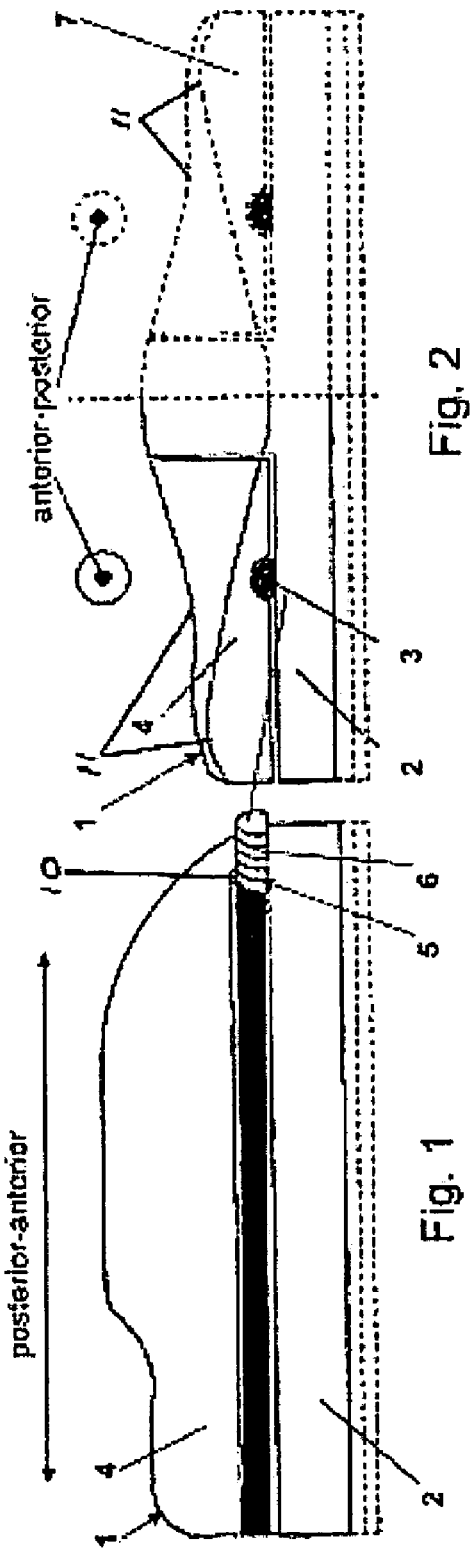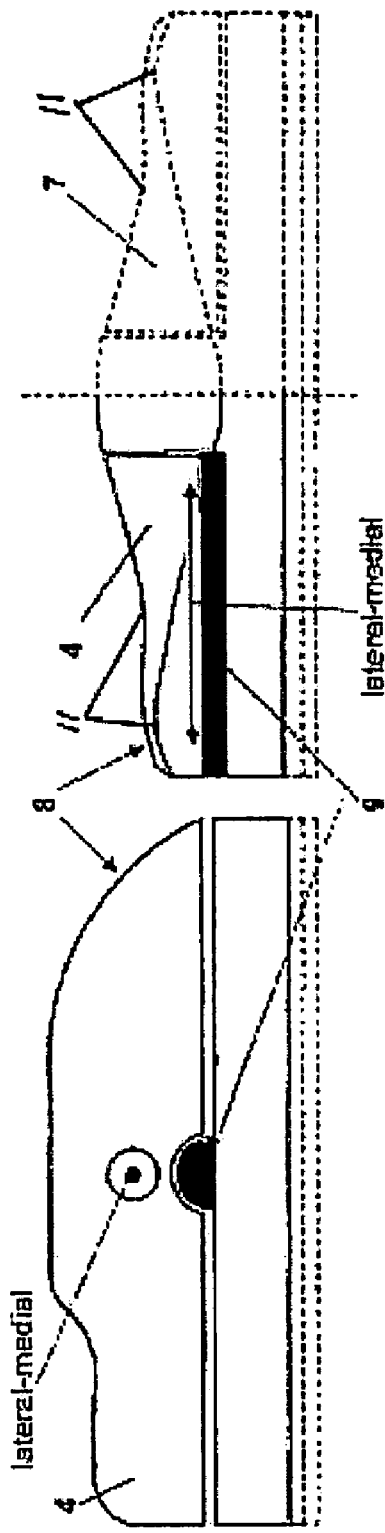

METHOD FOR DETERMINING AND ADJUSTING THE OPTIMAL RELATIVE POSITION OF A FUNCTIONAL SURFACE OF AN ARTIFICIAL JOINT

Priority is claimed to German Patent Application No. DE 10 2005 044 044.4, filed on Sep. 14, 2005, the entire disclosure of which is incorporated by reference herein.

The present invention relates to an apparatus for determining and adjusting the optimal relative position of at least one functional surface of an artificial joint, especially for use with an endoprosthesis for the human knee joint. Furthermore, the invention relates to a method to be used with the apparatus as well as to the use of implants that have the optimal shape and relative position.

BACKGROUND

Artificial joints, especially knee joints, have already been the subject matter of numerous publications. For instance, German patent specification DE 102 31 538 C1, which is incorporated by reference herein, describes an artificial joint as an endoprosthesis for the human knee joint, comprising a first joint compartment formed by a first condyle and a first socket, as well as a second joint compartment formed by a second condyle and a second socket whereby, opposite from the condyle, a convexity is present laterally on the tibia in the sagittal main functional plane while a concavity is present transversally, and whereby the two contact surfaces of the appertaining joint compartments have an offset in a main functional plane. This translates into a better range of motion for patients in a manner that approximates the natural range of motion.

WO 98/20816, which is incorporated by reference herein, relates to an artificial joint consisting of at least two artificial joint components with curved articulation surfaces, a curved contact line being formed on each of the articulation surfaces.

The artificial joints known from these sources achieve an optimal approximation of the natural range of motion.

However, the replacement of individual contact surfaces of human joints with functional surfaces of artificial joint elements has proven to be problematic in actual practice because the relative position and orientation of the artificial functional surfaces relative to the remaining functional surfaces, or of the artificial functional surfaces among each other, are of decisive significance for the range of motion that can be thus achieved. In actual practice, however, this is not dependent on the skill of the surgeon but rather on coincidence.

Publications likewise known from the state of the art are U.S. patent application no. 2005/0101966, world patent application WO 98/41152 A1, world patent application WO 2004/041097 A1, European patent application EP 14 02 855 B1 as well as U.S. Pat. No. 6,002,859. The entire disclosures of each of the aforesaid publications, are incorporated by reference herein.

SUMMARY OF THE INVENTION

An object of the present invention is to provide an apparatus for determining the optimal relative position of several functional surfaces. A further or alternate object is to provide a method for determining the optimal relative position of several functional surfaces.

The present invention provides an apparatus for determining the optimal relative position of several functional surfaces of a condyle and/or of a socket of a human and/or artificial joint, especially to be used with an endoprosthesis for the human knee joint, whereby the apparatus is furnished with a compartment that is moveable relative to a receptacle that can be detachably affixed to a human joint or bone region, so that a reference position of the compartment—relative to the receptacle—resulting from the motion of the knee joint can be established.

The relative position can be determined with a high degree of reliability and with little effort in that, prior to the permanent implantation, the apparatus is first detachably affixed as an adjustment aid whose compartment is moveable. In this manner, the subsequently induced joint motion causes a shift into the optimal relative position. This relative position can be recognized as a reference position on the apparatus, so that the artificial joint can be selected or adjusted on the basis of this reference position. The resulting relative position can optionally also be locked in place.

It is advantageous for the medial compartment, that is to say, the inner joint compartment consisting of the condyle and the socket, and for the outer compartment to be convex-convex in shape in the sagittal direction (main functional direction), but transversally, for the condyle to be convex and the tibia surface to be concave. These surfaces thus shaped can be optimally adjusted in a four-joint relationship relative to the ligament structures.

Advantageously, the contact structures in the transversal section each lie on the internal slopes.

For example, a vertical adjustment can be made by inserting several hollow inlays or else by using a screw mechanism or the like.

The compartment could be arranged so as to be moveable, for instance, by means of a ball-and-socket joint having several degrees of freedom. However, it is particularly advantageous if the compartment is arranged movably in the direction of two spatial axes, as a result of which it is easier to read out the reference position as X and Y coordinates.

To this end, it is especially advantageous for the compartment to be connected to the receptacle via a sliding guide, so that the relative position can be directly read from the moveable areas of the sliding guide. This can be combined with a snap-in mechanism. The sliding guide can also be configured in such a way that greater force has to be applied to overcome a frictional resistance in order to prevent the compartment from inadvertently moving back. Furthermore, the components can be arranged so that they are captive.

For instance, a suitable variant for this purpose is one in which the compartment has an especially groove-like recess into which a projection of the receptacle engages so as to reduce the amount of design work required.

Moreover, it has proven to be very promising for the reference position to be identified by a marking and for this marking to have a scale on the basis of which the suitable artificial joint or individual elements can be directly selected.

Another likewise especially practical variant of the present invention is achieved in that a sensor for electronic signal processing is associated with the marking so that the reference position thus established can undergo electronic data processing, thus simplifying the selection and adaptation of the artificial joint.

Furthermore, it is especially beneficial for the apparatus to have a sensor to detect the relative movement of the compartment with respect to the receptacle during the motion of the knee joint so that information can be acquired about the range of motion and thus about the reference position as a function of the angular position of the joint.

Fundamentally, the apparatus can be employed to determine the relative position of a single artificial functional surface relative to the remaining surface areas of the human joint. In contrast, another particularly practical variant is one in which the apparatus has at least two compartments that are movable with respect to each other. Here, the determination of the relative position is not limited to adjacent compartments, but rather, the relative position can also be determined in operatively connected compartments that are located opposite from each other.

The apparatus can be used in any desired joints. However, it is particularly advantageous for the apparatus to serve to adjust either a socket associated with the tibia on the inside or else the femur condyle on the outside of the tibia in the main functional plane, with a sagittally associated convexity and a transversally associated concavity.

The present invention also provides a method for determining a relative target position of an artificial joint element designed especially as an endoprosthesis for the human knee joint, in which method first of all, at least one compartment is removed and an apparatus that serves as an adjustment aid is detachably affixed, subsequent to which the knee joint is moved and the reference position resulting from the relative shift of the adjustment aid is established and serves as the basis for selecting and/or adjusting the artificial joint element to be implanted, after which the apparatus is removed in order to implant the artificial knee joint.

As a result, there is no need to use the joint parameters of the human joint in order to adjust and select the suitable artificial joint since the reference position can be easily read from the apparatus and can then be used directly to adjust and select the artificial joint elements.

Merely a simple motion of the joint induced by an assistant is sufficient for the reference position to be autonomously adjusted. In this context, it is especially advantageous for the knee joint to be completely flexed, especially during the operation, so that the reference position can be obtained.

According to another, particularly advantageous variant which involves repeating the method for determining the relative target position of several compartments of the condyle or of the socket, the relative positions of several or of all of the joint compartments can be adjusted without any problems.

For example, in order to determine the suitable compartment, the reference position is established as a correction variable and the joint compartments of the replacement joint are determined on the basis of the reference position.

BRIEF DESCRIPTION OF THE DRAWINGS

The invention allows various embodiments. For purposes of further elucidating its basic principle, two of these embodiments are depicted in the drawings and will be described below. The following is shown:

FIG. 1 a side view of an adjustment apparatus according to the invention with one degree of freedom; the side with the broken line represents the optional lateral or medial arrangement of the moveable compartment;

FIG. 2 a front view of the adjustment apparatus shown in FIG. 1;

FIG. 3 a side view of another adjustment apparatus entailing one degree of freedom; and FIG. 4 a front view of the adjustment apparatus shown in FIG. 3.

DETAILED DESCRIPTION

FIGS. 1 and 2 show a side view as well as a front view of an apparatus (designated by the reference numeral 1 in its entirety with all of the elements shown) for determining and adjusting the optimal position of a functional surface of an artificial joint and of the correspondingly shaped implant components of the artificial joint. The apparatus 1 is furnished with a compartment 4 that can be moved relative to a receptacle 2 that can be detachably affixed to a human joint or bone region by means of a sliding guide 3. A reference position of the receptacle 2, which is established relative to the compartment 4 during the surgery on the basis of the posterior-anterior motion of the knee joint, is determined by means of a marking 6 that has a scale 5. This creates the possibility of reading off the optimal position in order to apply this information to the dimensioning of the implant components and to the implant position. A sensor 10 for signal processing can be associated with the reading so that the reference position thus established can undergo data processing. In addition, the lateral compartment 4 can also be moved relative to a medial compartment 7 in order to improve the adjustability. Also shown are the internal slopes 11 of at least one of the condyle and the socket upon which a contact line in the transversal section lies.

In contrast, FIGS. 3 and 4 show a side view as well as a front view of another apparatus (designated by the reference numeral 8 in its entirety with all of the elements shown), the lateral compartment 4 and/or the medial compartment 7 being arranged so that they can be moved in the direction of two spatial axes—posterior-anterior as well as lateral-medial—in the manner of a compound table, by means of the sliding guide 3 shown in FIGS. 1 and 2 and by means of another sliding guide 9. The apparatus 8 is detachably affixed as an adjustment aid, whereby the lateral compartment 4 and/or the medial compartment 7 can move relative to the receptacle 2. In this manner, inducing the joint motion causes a shift into the optimal relative position, which can be recognized or locked in place as the reference position on the apparatus 8, so that the artificial joint can be selected or adjusted on the basis of this reference position.

What is claimed is:

1. A method for determining a relative target position of an artificial joint element of a knee joint having four compartments, each compartment including at least a portion of a condyle and a socket, the method comprising:

removing at least one compartment from the artificial knee joint;

temporarily replacing the at least one compartment with an adjustment aid, the adjustment aid including a receptacle and a further component disposed moveably relative to the receptacle, wherein the temporarily replacing includes detachably affixing the receptacle to a bone region on one side of the knee joint, wherein the further compartment cooperates with one of the four compartments remaining in the knee joint;

pivoting the knee joint so that the cooperation of the further compartment with the one of the four compartments causes the further compartment to shift relative to the receptacle;

establishing a reference position resulting from the relative shift of the artificial further compartment to the receptacle;

at least one of selecting and adjusting the artificial joint element to be implanted using the reference position; and removing the adjustment aid so as to enable an implantion of the artificial joint element.

2. The method as recited in claim 1, wherein the artificial joint element is an endoprothesis and the joint is a human knee joint.

3. The method as recited in claim 1, wherein the establishing of the reference position includes completely flexing the knee joint.

4. The method as recited in claim 1, further comprising repeating the steps so as to determine a further relative target position of further artificial joint elements.

5. The method as recited in claim 1, wherein the reference position is established as a correction variable.

6. The method as recited in claim 1, further comprising determining joint compartments of the artificial joint based on the reference position.

* * * * *